United States Patent
Lia et al.

(10) Patent No.: US 7,134,993 B2
(45) Date of Patent: Nov. 14, 2006

(54) METHOD AND APPARATUS FOR IMPROVING THE OPERATION OF A REMOTE VIEWING DEVICE BY CHANGING THE CALIBRATION SETTINGS OF ITS ARTICULATION SERVOS

(75) Inventors: Raymond A. Lia, Auburn, NY (US); Joshua L. Scott, Jordan, NY (US)

(73) Assignee: GE Inspection Technologies, LP, Lewiston, PA (US)

( * ) Notice: Subject to any disclaimer, the term of this patent is extended or adjusted under 35 U.S.C. 154(b) by 163 days.

(21) Appl. No.: 10/807,595

(22) Filed: Mar. 24, 2004

(65) Prior Publication Data
US 2005/0168571 A1    Aug. 4, 2005

Related U.S. Application Data

(63) Continuation-in-part of application No. 10/768,761, filed on Jan. 29, 2004.

(51) Int. Cl.
*A61B 1/00*    (2006.01)

(52) U.S. Cl. ..................................... 600/149

(58) Field of Classification Search ............... 600/101, 600/139, 149–150
See application file for complete search history.

(56) References Cited

U.S. PATENT DOCUMENTS

| | | | |
|---|---|---|---|
| 2,461,797 A | 2/1949 | Zwicky |
| 2,844,126 A | 7/1958 | Gaylord |
| 2,963,543 A | 12/1960 | Link et al. |
| 3,190,286 A | 6/1965 | Stokes |
| 3,557,780 A | 1/1971 | Sato |
| 3,610,231 A | 10/1971 | Takahashi et al. |
| 3,669,098 A | 6/1972 | Takahashi |
| 3,690,775 A | 9/1972 | Cousins |
| 3,694,094 A | 9/1972 | Low et al. |
| 3,799,151 A | 3/1974 | Fukaumi et al. |
| 3,892,228 A | 7/1975 | Mitsui |
| 4,108,221 A | 8/1978 | Freimuth et al. |
| 4,203,430 A | 5/1980 | Takahashi |
| 4,294,233 A | 10/1981 | Takahashi |
| 4,483,326 A | 11/1984 | Yamaka et al. |
| 4,503,842 A | 3/1985 | Takayama |
| 4,509,507 A | 4/1985 | Yabe |
| 4,559,928 A | 12/1985 | Takayama |
| 4,659,195 A | 4/1987 | D'Amelio et al. |

(Continued)

FOREIGN PATENT DOCUMENTS

EP    0078017    5/1983

(Continued)

*Primary Examiner*—John Leubecker
*Assistant Examiner*—Philip R Smith
(74) *Attorney, Agent, or Firm*—Wall Marjama & Bilinski LLP

(57) ABSTRACT

The present invention features a remote viewing device that is capable of improving its operation by removing slack in its control cables and/or by increasing the range of motion of its viewing head. In one embodiment, the method for improving the operation involves removing at least a portion of the slack in at least one control cable attached to a servo motor. The removal of at least a portion of the slack includes changing the position of a servo motor relative to a flexible tube termination block until a specified tension is encountered in at least one of the control cables. The method further includes determining first and second servo control signal values corresponding to no angular deflection and a specified deflection in a viewing head.

13 Claims, 6 Drawing Sheets

U.S. PATENT DOCUMENTS

| | | | |
|---|---|---|---|
| 4,680,931 A | 7/1987 | Jacobs | |
| 4,688,555 A | 8/1987 | Wardle | |
| 4,700,693 A | 10/1987 | Lia et al. | |
| 4,787,369 A | 11/1988 | Allred, III et al. | |
| 4,796,607 A | 1/1989 | Allred, III et al. | |
| 4,805,596 A | 2/1989 | Hatori | |
| 4,941,454 A * | 7/1990 | Wood et al. | 600/149 |
| 4,950,258 A | 8/1990 | Kawai et al. | |
| 4,996,974 A | 3/1991 | Ciarlei | |
| 5,018,506 A | 5/1991 | Danna et al. | |
| 5,019,121 A | 5/1991 | Krauter | |
| 5,060,632 A | 10/1991 | Hibino et al. | |
| 5,299,559 A | 4/1994 | Bruce et al. | |
| 5,359,994 A | 11/1994 | Krauter et al. | |
| 5,545,200 A | 8/1996 | West et al. | |
| 5,658,238 A | 8/1997 | Suzuki et al. | |
| 5,800,341 A | 9/1998 | McKenna et al. | |
| 5,904,667 A | 5/1999 | Falwell | |
| 5,944,690 A * | 8/1999 | Falwell et al. | 604/170.03 |
| 5,954,654 A | 9/1999 | Eaton et al. | |
| 5,966,210 A | 10/1999 | Rosow et al. | |
| 5,989,182 A | 11/1999 | Hori et al. | |
| 6,156,027 A | 12/2000 | West | |
| 6,261,226 B1 | 7/2001 | McKenna et al. | |
| 6,388,742 B1 | 5/2002 | Duckett | |
| 6,574,958 B1 | 6/2003 | MacGregor | |
| 6,595,914 B1 * | 7/2003 | Kato | 600/152 |
| 6,793,622 B1 * | 9/2004 | Konomura et al. | 600/152 |
| 2001/0037084 A1 | 11/2001 | Nardeo | |
| 2001/0043450 A1 | 11/2001 | Seale et al. | |
| 2003/0026702 A1 | 2/2003 | Yoo et al. | |
| 2003/0100818 A1 | 5/2003 | Lei et al. | |
| 2004/0054258 A1* | 3/2004 | Maeda et al. | 600/152 |
| 2004/0073083 A1* | 4/2004 | Ikeda et al. | 600/101 |
| 2004/0267093 A1 | 12/2004 | Miyagi et al. | |

FOREIGN PATENT DOCUMENTS

| | | |
|---|---|---|
| EP | 0543738 | 5/1993 |
| GB | 1296534 | 11/1972 |
| GB | 2143920 | 2/1985 |
| JP | 58189604 | 11/1983 |
| JP | 2-286882 | 11/1990 |
| WO | WO 95/03001 | 2/1995 |
| WO | WO 95/28872 | 11/1995 |

* cited by examiner

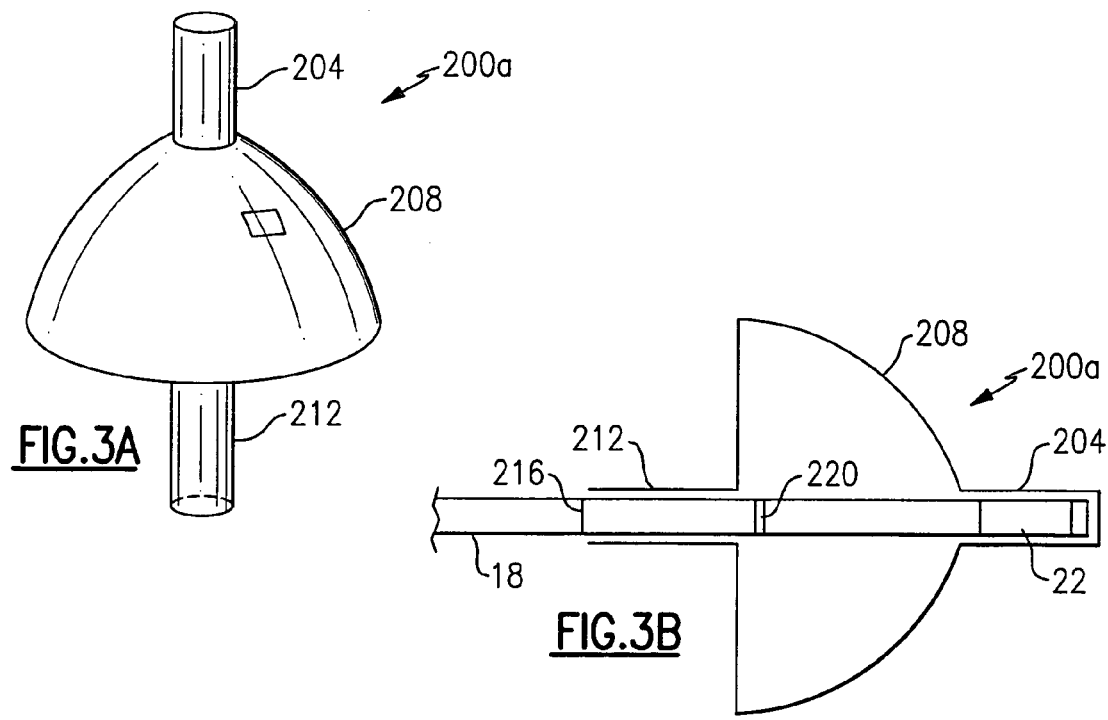
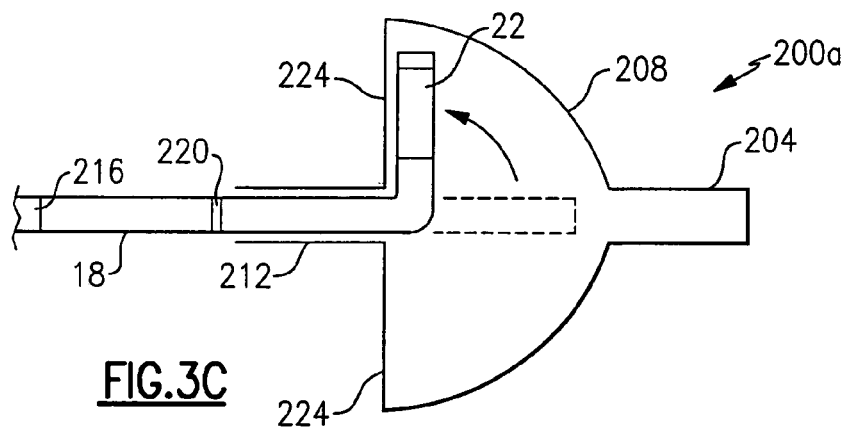
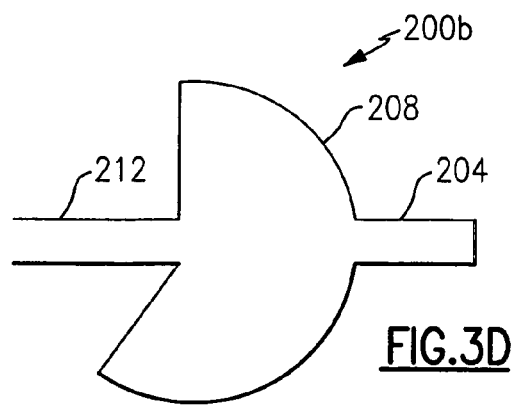

METHOD AND APPARATUS FOR IMPROVING THE OPERATION OF A REMOTE VIEWING DEVICE BY CHANGING THE CALIBRATION SETTINGS OF ITS ARTICULATION SERVOS

CROSS-REFERENCE TO RELATED APPLICATIONS

This application claims priority to and is a continuation-in-part of co-pending U.S. patent application Ser. No. 10/768,761 entitled Remote Video Inspection System, filed Jan. 29, 2004, which application is incorporated herein by reference in its entirety.

FIELD OF THE INVENTION

The invention relates generally to a system and method for improving the operation of a remote viewing device. More particularly the invention relates to changing the calibration settings of the remote viewing device's articulation servos to remove slack in the control cables and/or increase the range of motion of the viewing head.

BACKGROUND

Borescopes, endoscopes, fiberscopes and the like (herein after generally referred to as remote viewing devices) are widely used to provide visual inspection of physically difficult to reach or inhospitable environments. The movement of remote viewing devices is frequently controlled by articulation servos that vary the tensions in control cables. The change in tensions in the control cables guides the movement of the remote viewing device's viewing head.

Over the life of a remote viewing device, numerous factors including cable stretch and increased friction and stiffness can lead to imprecise operation and a decrease in the viewing head's range of motion. Some previous industry responses to these problems require that the remote viewing device be disassembled by a specialized technician. This can in turn require that the remote viewing device be returned to the manufacturer for processing.

What is needed is a system that is easily executable by a standard operator to remove cable stretch and increase a viewing head's range of motion.

SUMMARY OF THE INVENTION

In one aspect, the invention features a method for improving the operation of a remote viewing device. The method comprises removing at least a portion of slack from at least one control cable attached to a servo motor. The removal of the at least a portion of slack includes at least changing a distance between the servo motor and a flexible tube termination block until a specified tension is encountered in the at least one control cable. The method also comprises fixing the servo motor where the specified tension is encountered and determining a first servo control signal value corresponding to no angular deflection in a viewing head of the remote viewing device. In addition the method comprises increasing the viewing head's range of motion. The process of increasing the viewing head's range of motion includes at least determining a second servo control signal value corresponding to a first angular deflection in the viewing head.

In one embodiment the method further comprises determining a third servo control signal value corresponding to a second angular deflection in the viewing head of the remote viewing device. In another embodiment the method further comprises storing the value of the first and second servo control signal values in a memory of a control unit of the remote viewing device. In an additional embodiment, the method further comprises placing a recalibration cap over the viewing head in a first position, wherein the recalibration cap in the first position fixes the viewing head in a non-deflected position. In a further embodiment, determining a second servo control signal value includes: placing a recalibration cap over the viewing head in a second position, wherein the recalibration cap in the second position allows the viewing head to deflect a first number of degrees; and rotating the viewing head a first number of degrees until it is in contact with the recalibration cap. In yet another embodiment, the method further includes rotating the viewing head until imaging optics in the viewing head view a predetermined target.

In yet an additional embodiment, the method further comprises placing a first recalibration cap over the viewing head, wherein the first recalibration cap fixes the viewing head in a non-deflected position. In yet a further embodiment, the determining a second servo control signal value includes: placing a second recalibration cap over the viewing head, wherein the second recalibration cap allows the viewing head to deflect a first number of degrees; and rotating the viewing head the first number of degrees until it is in contact with the second recalibration cap. In still another embodiment, the first and second servo control signal values are used to recalibrate the operation of the remote viewing device to increase the viewing head's range of motion.

In still an additional embodiment, the recalibration includes changing a stroke of and/or a force applied by the servo motor. In still a further embodiment, the method further comprises determining an extrapolated servo control signal value for an arbitrary deflection in the viewing head, the determining the extrapolated servo control signal value using at least the first and second servo control signal values. In still yet another embodiment, the at least one control cable is a plurality of control cables and the determining a first servo control signal value that corresponds to no angular deflection in the viewing head of the remote viewing device includes at least equalizing tensions in the plurality of control cables. In still yet an additional embodiment, the remote viewing device is one of: a borescope, a fiberscope, or an endoscope.

In another aspect, the invention features a system for improving the operation of a remote viewing device. The method comprises a remote viewing device control unit; a remote viewing device viewing head; a remote viewing device flexible tube connected at a proximal end to the control unit and at the distal end to the viewing head; and at least one servo motor located in the control unit and connected to at least one control cable that passes through the flexible tube and is attached to the viewing head, a distance between the at least one servo motor and a flexible tube termination block capable of being varied to remove at least a portion of slack in the at least one control cable.

In one embodiment, the system comprises at least one servo motor support rail attached to a support structure in the remote viewing device control unit; a spring connected to the support structure and the at least one servo motor; a top groove plate attached to the at least one servo motor; and a bottom groove plate coupled to an engagement screw, wherein the engagement screw engages and disengages the top and bottom groove plates such that when the top and bottom groove plates are engaged the at least one servo motor is held in a fixed position and when the top and bottom groove plates are disengaged the at least one servo motor is moved by the spring on the servo motor support rail until a specified tension is encountered in the at least one control cable. In another embodiment, the adjustment screw is manually adjusted through an opening in the control unit. In a further embodiment, the adjustment screw is automatically adjusted by an adjustment servo motor.

In yet another embodiment, the system further comprises at least one track attached to a support structure in the remote viewing device control unit; at least one rail attached to the at least one servo motor or flexible tubing termination block, the at least one rail movably connected to the at least one track; and an adjustment screw, wherein the adjustment screw changes the location of the at least one servo motor along the track allowing a specified tension to be achieved in the at least one control cable. In yet an additional embodiment, the adjustment screw is manually adjusted through an opening in the control unit. In yet a further the adjustment screw is automatically adjusted by an adjustment servo motor.

In still another embodiment, the system further comprises at least one track attached to a support structure in the remote viewing device control unit; at least one rail attached to a flexible tubing termination block, the at least one rail movably connected to the at least one track; and an adjustment screw, wherein the adjustment screw changes the location of the flexible tubing termination block along the track allowing a specified tension to be achieved in the at least one control cable. In still another embodiment, the flexible tube termination block is a threaded flexible tube termination block that is placed in a threaded housing, rotation of the threaded flexible tube termination block changing the distance between the at least one servo motor and the threaded flexible termination block. In still an additional embodiment, the system further comprises a recalibration cap including at least a distal non-deflection region, a middle deflection region, and a proximal clasping region, wherein the distal non-deflection region is capable of maintaining the viewing head in a substantially non-deflected position and the middle deflection region permits the viewing head to deflect a specified number of degrees.

In an additional aspect, the invention features a system for improving the operation of a remote viewing device. The system comprises a remote viewing device control unit including at least a microprocessor, a memory unit, a servo control unit, and a servo motor, the microprocessor operatively coupled to the memory unit and the servo control unit and the servo motor operatively coupled to the servo motor control unit; a remote viewing device viewing head; a remote viewing device flexible tube connected at a proximal end to the control unit and at the distal end to the viewing head; at least one control cable connected to the servo motor and the remote viewing device viewing head and passing through the remote viewing device flexible tube; and a software routine stored in the memory unit, the software routine directing the microprocessor and the servo control unit to remove slack from the at least one control cable.

In another embodiment, the removal of slack includes at least: moving the servo motor to a first location where a specified tension is encountered in at least one of the at least one control cables; and fixing the servo motor at the first location thereby establishing a fixed relative distance between the servo motor and the flexible tube termination block.

In a further aspect, the invention features a system for improving the operation of a remote viewing device. The system comprises a remote viewing device control unit including at least a microprocessor, a memory unit, a servo control unit, and a servo motor, the microprocessor operatively coupled to the memory unit and the servo control unit and the servo motor operatively coupled to the servo motor control unit; a remote viewing device viewing head; a remote viewing device flexible tube connected at a proximal end to the control unit and at the distal end to the viewing head; at least one control cable connected to the servo motor and the remote viewing device viewing head and passing through the remote viewing device flexible tube; and a software routine stored in the memory unit, the software routine directing the microprocessor and the servo control unit to extend a range of motion of the viewing head. In one embodiment, the extending the range of motion of the viewing head includes at least determining servo control signal values corresponding to a deflected and a non-deflected location of the viewing head.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIGS. 3A, 3B, 3C, and 3D show embodiments and views of a recalibration cap constructed in accordance with the principles of the invention.

DETAILED DESCRIPTION

The present invention features a remote viewing device (a remote viewing device refers generally to borescopes, fiberscopes, endoscopes, and the like) that is capable of improving its operation by removing slack in its control cables and/or increasing the range of motion of its viewing head. The procedure for improving the operation involves recalibrating the control cable servo motors and can involve changing the stroke of and/or the force applied by the servo motors. The procedure is significantly automated and can be performed without the need for a specialized recalibration technician.

Figure 1A:
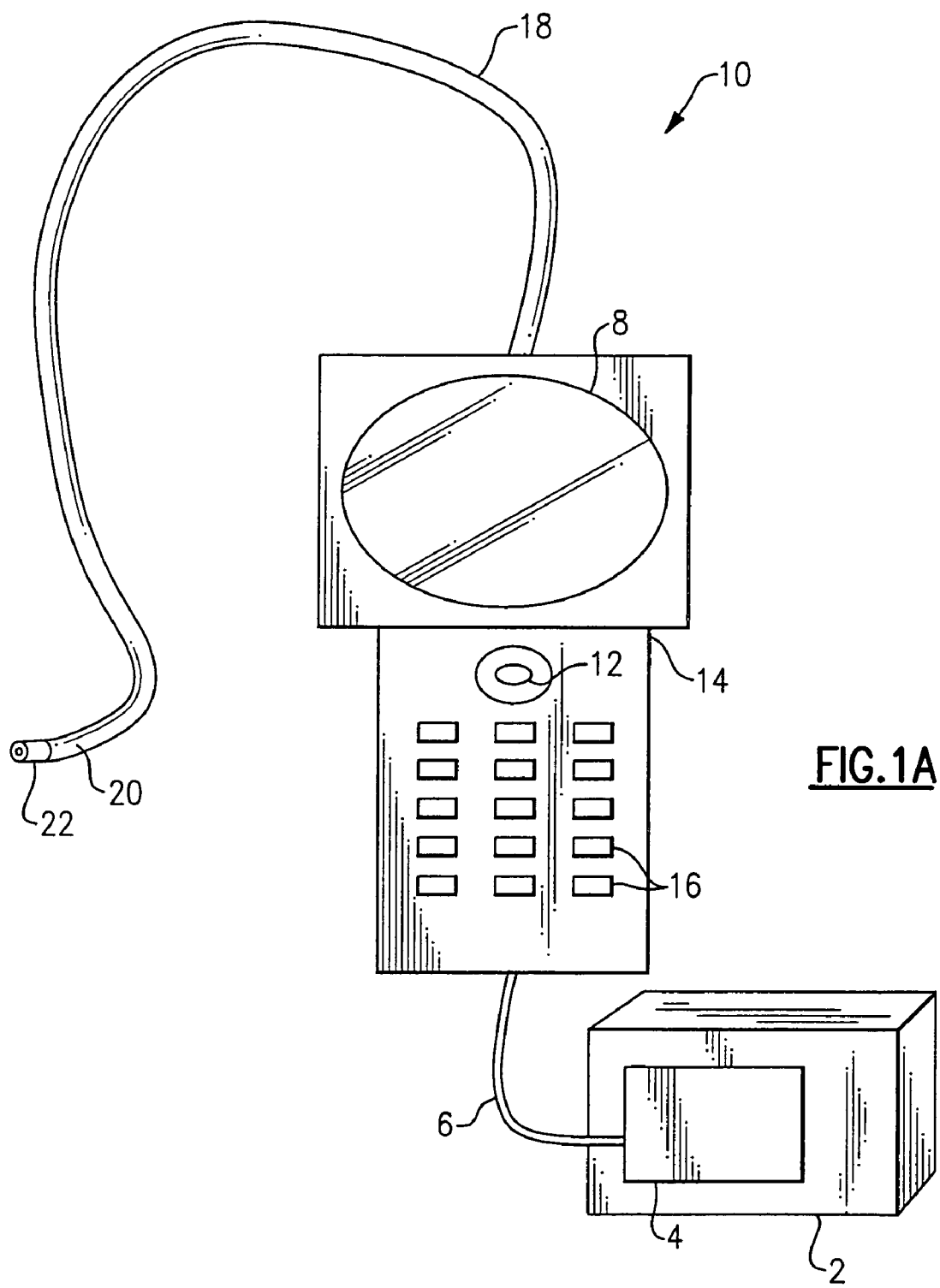
FIG. 1A is an exemplary remote viewing device constructed in accordance with the principles of the invention.

Referring to FIG. 1A, a typical remote viewing device 10 (a borescope in the illustrative embodiment) according to the invention is illustrated, such as is sold by Everest VIT® of Flanders, N.J. Such a device could include, as shown in the illustrative embodiment, a portable shipping/operating case 2, which includes a power supply 4 for the device and a light source, such as a metal halide arc lamp (not shown).

The shipping/operating case 2 is shown in operative communication with a control unit 14 by means of a tethered cable 6. The control unit 14 can include, by way of example, a set of user interfaces including a visual interface 8 (such as a LCD monitor that displays images seen by the remote viewing device 10 and displays control and configuration information to the user), a joystick control 12 (for articulating a distal end 20 of the remote viewing device 10), and a set of actuatable or depressible buttons 16 (for accessing measurement and digital imaging controls associated with the remote viewing device 10). The control unit 14 also is connected to a flexible tube 18, which terminates in a distal end 20. As used herein, the term "distal" shall mean "in the direction of the viewing head of the boroscope, furthest from the control unit 14." The distal end 20 of the flexible tube 18 is shown attached to a viewing head 22. The flexible tube 18 can be sized according to the desired application, by varying a diameter and a length of the flexible tube 18. The flexible tube 18 can include, for example, a durable tungsten braid overlaying a stainless steel monocoil for crush resistance, and one or more layers of a polyurethane sealant for protection from liquids and vapors. The interior of the flexible tube 18 (not shown) can include standard imager lines and communication/control means, such as fiber-optic cables and articulation wires extending through the tube to the control unit 14 permitting illumination from the light source and articulation control of the flexible tube 18 via the joystick 12.

Figure 1B:
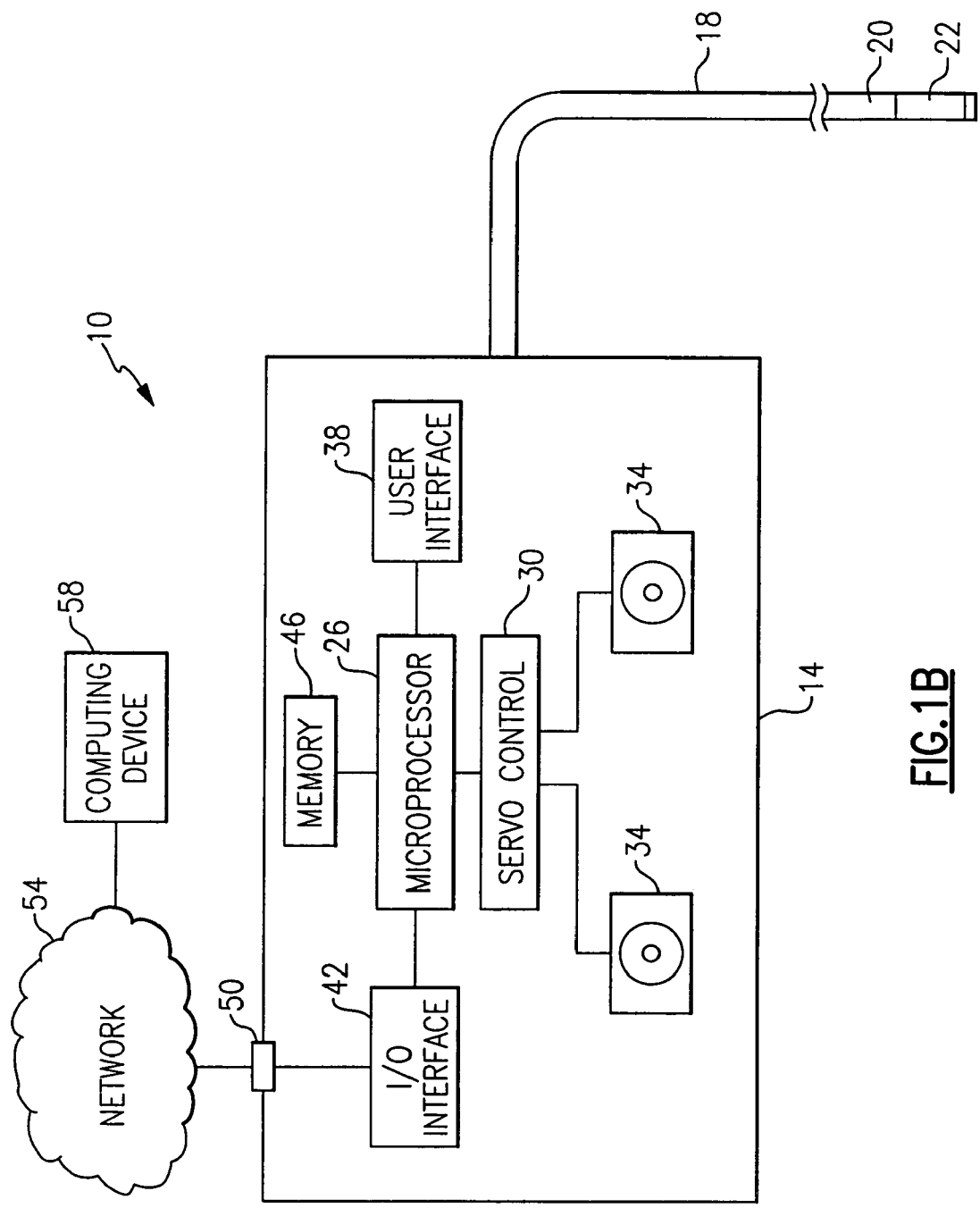
FIG. 1B is a block diagram of the control unit portion of the remote viewing device shown in FIG. 1A.

FIG. 1B shows additional details of the control unit 14 of FIG. 1 including its interface with external networks and devices. As indicated above, the remote viewing device 10 includes a control unit 14, a flexible tube 18, and a viewing head 22. The details of the control unit 14 are shown in block diagram form and include a microprocessor 26 that is operatively coupled to a servo control unit 30 that is in turn operatively coupled to the servo motors 34. In typical operation each servo motor is responsible for the motion of the viewing head 22 in one of two perpendicular directions. The microprocessor 26 is also operatively coupled to user interfaces 38 (such as the visual interface 8, the joystick control 12, and the buttons 16), an I/O interface 42, and a memory unit 46. In various embodiments, the memory unit 46 is Random Access Memory, Read Only Memory, Programmable Read Only Memory, Erasable Programmable Read Only Memory and the like. In further embodiments, additional memory units 46 are coupled to the microprocessor 26. The I/O interface 42 is operatively coupled to an I/O port 50. In the current embodiment the I/O port 50 is shown operatively coupled to a network 54 to which is connected at least one computing device 58, such as a server or a personal computer. In alternative embodiments, the control unit 14 can be directly connected to the computing device 58 or can function without any external network or computer connection.

Figure 2A:
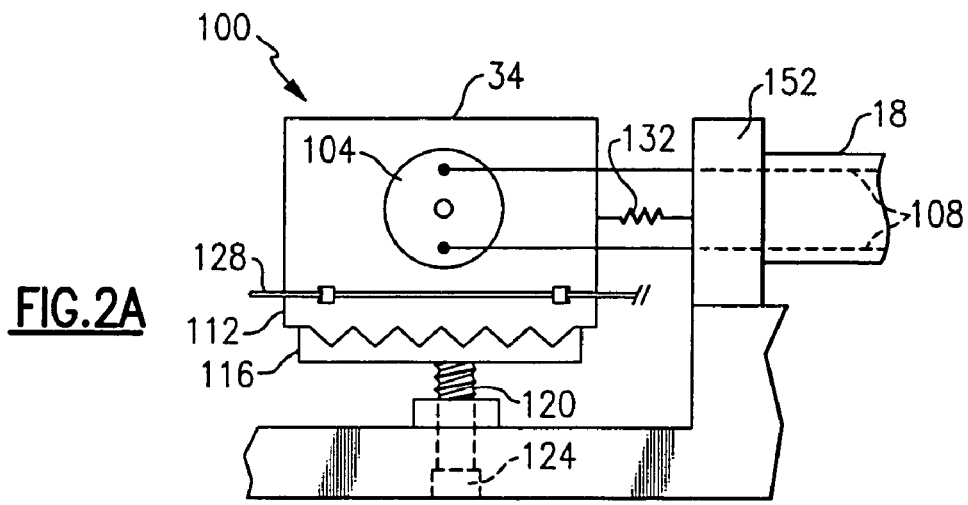
FIGS. 2A, 2B and 2C show embodiments of a servo motor mounting and adjustment system constructed in accordance with the principles of the invention.
Figure 2B:
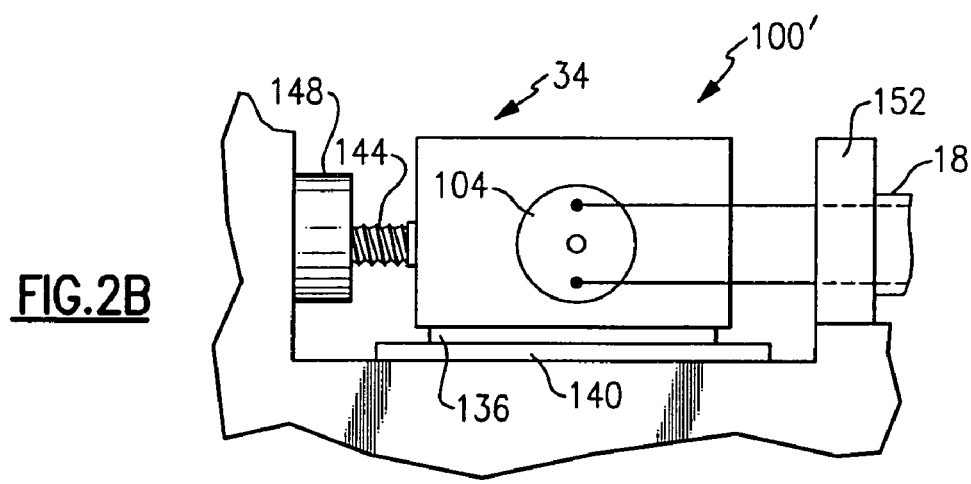
Figure 2C:
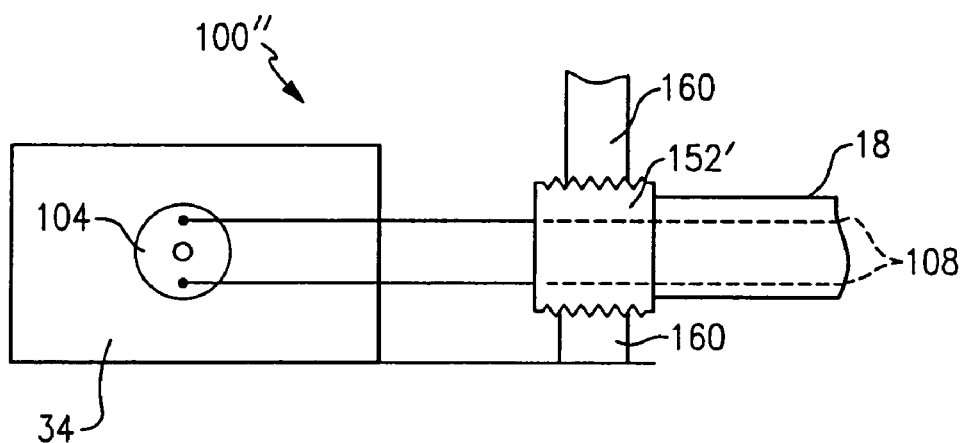

FIGS. 2A, 2B, and 2C show cut-away drawings of three embodiments of a servo motor mounting and adjustment system 100, 100', 100" that are used to remove a first amount of cable stretch from the control cables of the remote viewing device. The mounting and adjustment systems 100, 100', 100" provide details regarding the structures surrounding the servo motors 34 in the control unit 14. In the systems 100, 100', 100", a pulley 104 is attached to two control cables 108 that pass through a flexible tube termination block 152 into the flexible tube 18 until connecting to the viewing head 22. Motion of the viewing head is achieved by rotating the pulley 104 and creating different tensions in the control cables 108. In operation the first amount of cable stretch is removed by changing the relative position between the servo motor 34 and the flexible tube termination block 152.

The mounting and adjustment system 100 of FIG. 2A includes a servo motor 34 and top 112 and bottom 116 groove plates. The bottom groove plate 116 is connected to an engagement screw 120 that is accessible via an opening 124. By rotating the engagement screw 120, the top 112 and bottom 116 groove plates can be engaged or disengaged. When disengaged, the servo motor 34 rides freely on a support rail 128 and is pushed by a light spring 132. The servo motor is moved by the spring 132 until a specified resistance is encountered from the control cables 108. The support rail 128 is attached at either end to support structures 130, only one of which is shown in FIG. 2A. In an alternative embodiment of the mounting and adjustment system 100, the engagement screw 120 is attached to a servo motor, not shown, that controls the engagement or disengagement of the top 112 and bottom 116 groove plates.

The mounting and adjustment system 100' of FIG. 2B includes a servo motor 34, rails 136 connected to a track 140, and an adjustment screw 144. The adjustment screw 144 is connected to a servo motor 148 operatively coupled to the servo control unit 30 shown in FIG. 1. Rotation of the adjustment screw 144 causes the servo motor 34 to move towards and away from the servo motor 148 as the rails 136 move along the track 140. In an alternative embodiment not shown, the adjustment screw 144 is not connected to a servo motor and is instead accessible through an opening in the control unit 14.

The mounting and adjustment system 100" of FIG. 2C includes a servo motor 34 and a threaded flexible tube termination block 152' that is placed in a corresponding threaded housing 160. In operation, rotation of the threaded flexible tube termination block 152' causes the relative position between the servo motor 34 and the threaded flexible tube termination block 152' to change thereby changing the tension in the control cables 108. In an alternative embodiment not shown, the flexible tube termination block 152 is placed on rails that move along a track. In this embodiment, the relative position between the flexible tube termination block 152 and the servo motor 34 is achieved by rotating an adjustment screw connected to the flexible tube termination block 152.

In alternative embodiments (not shown) of the mounting and adjustment systems 100, the servo motor 34 and/or the flexible tube termination block 152 are moveably attached to a housing. In addition, the servo motor 34 and/or the flexible tube termination block 152 are attached to a spring loaded system that is actuatable by depressing a button or a similar interface mechanism. When actuated, the spring loaded system creates a specified tension in at least one of the control cables. In one embodiment, the specified tension is created by the spring loaded system changing the relative distance between the servo motor 34 and the flexible tube termination block 152.

Figure 4:
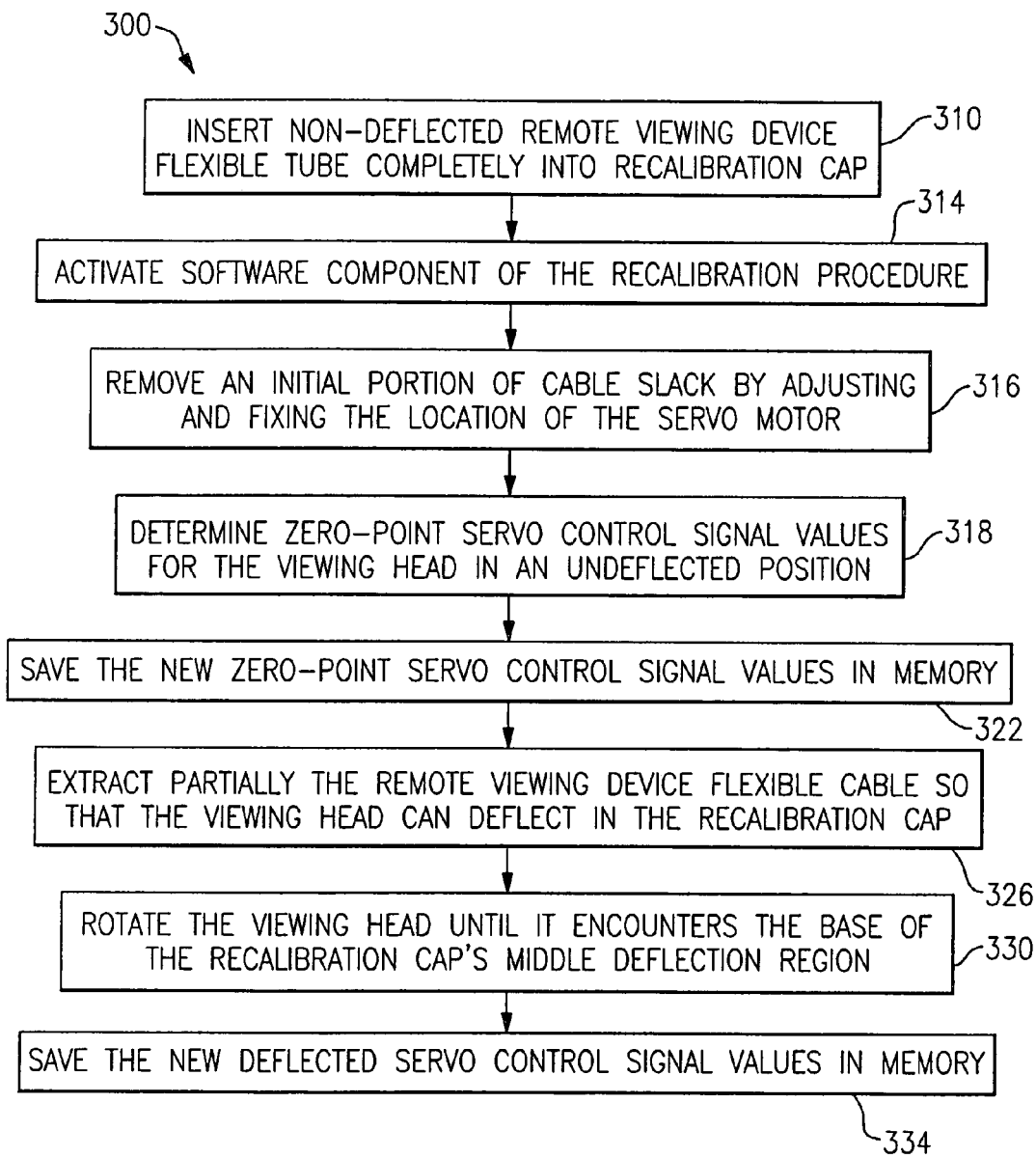
FIG. 4 is a flow-chart illustrating an embodiment of a recalibration procedure according to the principles of the invention.

FIGS. 3A, 3B, 3C and 3D show various views of recalibration caps 200a and 200b (generally 200) used in accordance with the invention. FIG. 3A shows a perspective view of the recalibration cap 200a. The recalibration cap 200a has a distal non-deflection region 204, a middle deflection region 208, and a proximal clasping region 212. FIGS. 3B, 3C and 3D are cut-away drawings through the middle of the recalibration caps 200a, 200b. FIG. 4 is a flow-chart that summarizes the recalibration procedure 300 involved in improving the operation of the remote viewing device 10.

Figure 5:
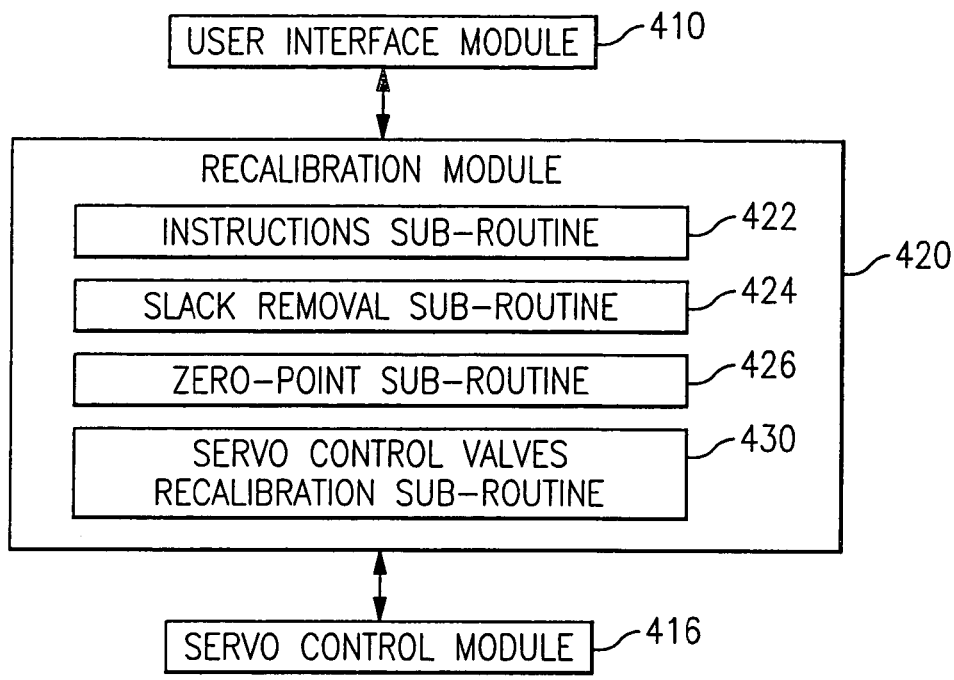
FIG. 5 shows a block diagram of a software program constructed in accordance with the invention.

FIG. 5 shows the components of the illustrative software program 400 that contains software routines that in some embodiments direct the remote viewing device 10 to automatically perform operations required for the recalibration procedure 300. The software program 400 includes a user interface module 410, a servo-control module 416, and a recalibration module 420. The recalibration module 420 includes an instructions sub-routine 422, a slack-removal sub-routine 424, a zero-point sub-routine 426, and a servo control values recalibration sub-routine 430. The user interface module 410 and the servo control module 416 can be specific to the recalibration procedure 300 or can be part of the general software routines used in controlling the operation of the remote viewing device 10. The operation of the various modules and sub-routines is discussed in more detail below with respect to the recalibration procedure 300. In alternative embodiments, the software program 400 is separated into different functional blocks than those specified by the modules and sub-routines above.

In one embodiment as part of the recalibration procedure 300, a user inserts (step 310) a non-deflected flexible tube 18 into the recalibration cap 200a until the distal end of the viewing head 22 is enclosed within the distal non-deflection region 204. This configuration is shown in FIG. 3B. The extent of the flexible tube 18 that must be inserted into the recalibration cap 200a is indicated by the presence of a mark 216 on the flexible tube 18. The gaps in FIG. 3B between the viewing head 22 and the non-deflection region 204 and between the flexible tube 18 and the proximal clasping region 212 are not necessarily to scale. In one embodiment, the inner diameter of the non-deflection region 204 and the proximal clasping region 212 are close fitting. As an illustrative example, the tolerance between the inner diameter of the non-deflection region 204 and the outer diameter of the viewing head 22 or the tolerance between the proximal clasping region 212 and the flexible tube 18 can be on the order of 0.010 inches. In additional embodiments, the non-deflection region 204 is tapered so that the viewing head 22 is nested tightly. In an alternative embodiment not shown, the proximal clasping region 212 includes a constricting strap or clasp that is used to tighten the proximal clasping region 212 around the flexible tube 18 once it has been inserted into the recalibration cap 200.

The software program 400 is stored in the memory unit 46 and is activated (step 314) by the user through the user interface 38. As part of the current embodiment, the instructions sub-routine 422 can send to the user interface 38 via the user interface module 410 instructions for the user regarding any step in the recalibration procedure 300 requiring user action. For example after pressing a recalibration button 16 or selecting a recalibration procedure via the user interface 38, the user can be instructed as to the proper insertion of the flexible tube 18 into the recalibration cap 200. Once inserted, the user is then instructed to notify the software program 400 so that the recalibration procedure can continue. In alternative embodiments, the software components are downloaded and/or initiated from the network or directly connected computing device 58. In an additional alternative embodiment not shown, the electronic operations of the recalibration procedure 300 are directly encoded in a specially designed integrated circuit.

An initial portion of the slack in the control cables 108 is removed (step 316) in one embodiment using the servo mounting and adjustment system 100 shown in FIG. 2A. In this embodiment, the top 112 and bottom 116 groove plates are separated via rotation of the engagement screw 120. With the plates 112, 116 separated, the spring 132 moves the servo motor 34 until it is restrained by a specified tension in at least one of the control cables 108. In this embodiment, the spring 132 is chosen to have a low spring constant so that the servo motor 34 stops moving as soon as a weak restraining pull is encountered from at least one the control cables 108. This weak restraining pull is encountered when the slack from at least one of the control cables 108 has been removed. The servo motor is next locked in this new position by reengaging the top 112 and bottom 116 groove plates. As discussed above, the movement of the bottom groove plate can be controlled via the external opening 124 or via a servo motor. If a servo motor is employed, the process of removing an initial portion of the slack in the control cables 108 can be performed automatically by the slack removal sub-routine 424 that employs the servo control module 416 to control the operation of the servo motor.

In an alternative embodiment, the initial portion of the slack in the control cables 108 is automatically removed using the servo mounting and adjustment system 100' shown in FIG. 2B. In this embodiment, the slack removal sub-routine 424 employs the servo control module 416 to direct the servo motor 148 to rotate the adjustment screw 144 until a slight increase in torque is required. This slight increase in torque corresponds to the slack of at least one of the control cables 108 having been removed and a specified tension existing in at least one of the control cables 108. The servo motor is next locked in this new position by maintaining the current setting of the servo motor 148. In an additional alternative embodiment, the initial slack in the control cables 108 is removed manually by accessing the adjustment screw 122 through the optional opening discussed above with respect to FIG. 2B. In this embodiment, a user rotates the adjustment screw 144 until a slight increase in the required torque is encountered.

The zero-point settings for the servo motors 34 corresponding no deflection in the viewing head 22 are determined (step 318) by rotating the servo motors 34 until each of the pair of the control cables 108 is equally taunt. In one embodiment, this operation is performed by the zero-point sub-routine 426. If the control cables 108 have stretched different amounts, then the initial removal of slack achieved during step 316 would have left slack in one of the control cables 108. As part of determining the zero-point setting, the servo motors 34 are rotated until their rotation in either direction requires the same increase in torque. This corresponds to the viewing head 22 being undeflected with each of the control cables 108 being equally taunt. The new zero-point servo control signal values are then stored (step 322) in memory 46. In an alternative embodiment not shown in which each control cable is attached to its own servo motor 34, substantially all of the slack in each control cable could be removed by rotating the servo motor 34 until a specified increase in torque was required. In this embodiment, the servo motors 34 would not need the mounting and adjustment systems 100 and 100' and the step 316 for removing an initial portion of the control cable slack would not be necessary.

The process of removing an initial portion of the control cable slack (step 316) and/or the process of determining the servo motors' 34 zero-point settings (step 318) are performed in one embodiment with a recalibration cap 200 secured over the viewing head 22. In an alternative embodiment, the user simply places the viewing head 22 in an undeflected position through visual inspection before performing the steps 316 and 318.

As shown in FIG. 3C, the flexible tube 18 is partially extracted (step 326) from the recalibration cap 200a until the markings 220 are adjacent to the base of the proximal clasping region 212. Once secured in this position, viewing head 22 is rotated (step 330) until it encounters the base 224 of the middle deflection region 208. FIG. 3C shows the base of the middle deflection region 208 forming an angle of approximately ninety degrees with the proximal clasping region 212. In alternative embodiments, the angle can be a different number of degrees or the angle can vary in steps around the axis of the recalibration cap. FIG. 3D shows an example of a recalibration cap 200b in which the angle is different for each half of the recalibration cap 200b.

Referring again to FIG. 3C, the servo motors 34 are rotated until a specified increase in torque is encountered corresponding to the viewing head 22 beginning to press against the base 224 of the middle deflection region 208. In an alternative embodiment, the viewing head 22 is rotated until imaging optics in the viewing head 22 view a predetermined target such as a marking placed at a specified location in the recalibration cap 200. The deflected servo control signal values of the servo control unit 30 corresponding to the viewing head deflected the specified number of degrees are stored (step 334) in memory 46.

Using the zero-point and the deflected servo control signal values, the remote viewing device 10 is able to extrapolate the servo control signal values required to produce an arbitrary deflection in the viewing head 22. These new servo control values can include changing the stroke and/or force applied by the servo motors 34. In one embodiment, the servo control signal values for a discrete set of closely spaced angular deflections are calculated and stored in a table in memory 46. In an alternative embodiment, the zero-point and deflected servo control signal values are used as parameters for a predefined algorithm that generates a servo control signal value for each input angular deflection. For example, in one embodiment, the predefined algorithm is an experimentally determined linear or non-linear curve fitting procedure. In an alternative embodiment, the servo control signal values corresponding to a plurality of angular deflections are measured and used to calculate the servo control signal values corresponding to an arbitrary angular deflection.

In one embodiment the procedures required to recalibrate the servo control values, including the rotation of the viewing head 22 and the calculation of arbitrary servo control values, are directed by the servo control values recalibration sub-routine 430.

Figure 6:
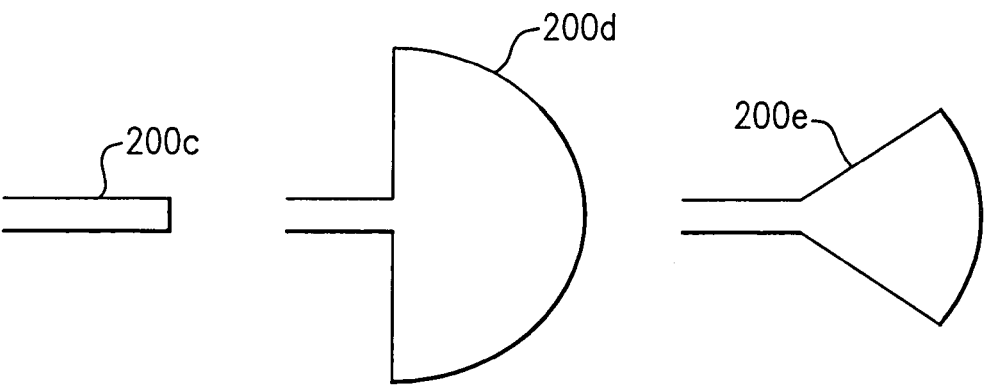
FIG. 6 shows cross-sectional views of recalibration caps constructed in accordance with the principles of the invention.

FIG. 6 shows cross sections of recalibration caps 200c, 200d, 200e that are used in an alternative embodiment where each step in the procedure 300 requiring a different angular deflection in the viewing head 22 employs a different recalibration cap. The recalibration cap 200c is employed when no angular deflection in the viewing head 22 is required whereas the recalibration caps 200d and 200e are employed when a specified angular deflection is required.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method for improving the operation of a remote viewing device, the method comprising:

removing at least a portion of slack from at least one control cable attached to a servo motor, the removing at least a portion of slack including at least changing a distance between the servo motor and a flexible tube termination block until a specified tension is encountered in the at least one control cable;

fixing the servo motor where the specified tension is encountered;

determining a first servo control signal value corresponding to no angular deflection in a viewing head of the remote viewing device;

determining a second servo control signal value corresponding to a first angular deflection in the viewing head; and increasing the viewing head's range of motion by recalibrating the operation of the remote viewing device based on at least the first servo control value and the second servo control signal value.

2. The method according to claim 1 further comprising determining a third servo control signal value corresponding to a second angular deflection in the viewing head of the remote viewing device.

3. The method according to claim 1 further comprising storing the value of the first and second servo control signal values in a memory of a control unit of the remote viewing device.

4. The method according to claim 1 further comprising placing a recalibration cap over the viewing head in a first position, wherein the recalibration cap in the first position fixes the viewing head in an undeflected position.

5. The method according to claim 4 wherein the determining a second servo control signal value includes:

placing a recalibration cap over the viewing head in a second position, wherein the recalibration cap in the second position allows the viewing head to deflect a first number of degrees; and rotating the viewing head a first number of degrees until it is in contact with the recalibration cap.

6. The method according to claim 4 wherein the determining a second servo control signal value includes:

placing a recalibration cap over the viewing head in a second position, wherein the recalibration cap in the second position allows the viewing head to deflect a first number of degrees; and rotating the viewing head until imaging optics in the viewing head view a predetermined target.

7. The method according to claim 1 further comprising placing a first recalibration cap over the viewing head, wherein the first recalibration cap fixes the viewing head in an undeflected position.

8. The method according to claim 7 wherein the determining a second servo control signal value includes:

placing a second recalibration cap over the viewing head, wherein the second recalibration cap allows the viewing head to deflect a first number of degrees; and rotating the viewing head the first number of degrees until it is in contact with the second recalibration cap.

9. The method according to claim 1 wherein the recalibration includes changing a stroke of the servo motor.

10. The method according to claim 1 wherein the recalibration includes changing a force applied by the servo motor.

11. The method according to claim 1 further comprising determining an extrapolated servo control signal value for an arbitrary deflection in the viewing head, the determining the extrapolated servo control signal value using at least the first and second servo control signal values.

12. The method according to claim 1 wherein the at least one control cable is a plurality of control cables and the determining a first servo control signal value that corresponds to no angular deflection in the viewing head of the remote viewing device includes at least equalizing tensions in the plurality of control cables.

13. The method according to claim 1 wherein the remote viewing device is one of: a borescope, a fiberscope, or an endoscope.

* * * * *